United States Patent [19]
Cartmell et al.

[11] Patent Number: 5,489,262
[45] Date of Patent: Feb. 6, 1996

[54] TRANSPARENT HYDROGEL WOUND DRESSING WITH RELEASE TAB

[75] Inventors: James V. Cartmell, Xenia; Wayne R. Sturtevant, Centerville; William E. Bausmith, III, Batavia; Michael L. Wolf, West Milton, all of Ohio

[73] Assignee: New Dimensions in Medicine, Inc., Dayton, Ohio

[21] Appl. No.: 435,298

[22] Filed: May 5, 1995

Related U.S. Application Data

[62] Division of Ser. No. 68,633, May 27, 1993, Pat. No. 5,423,737.

[51] Int. Cl.$^6$ ..................................................... A61F 13/00
[52] U.S. Cl. .................. 602/57; 602/48; 602/52; 602/58; 602/900; 206/440; 206/441
[58] Field of Search ................... 602/52, 57, 900; 156/266–271, 289; 206/440, 441

[56] References Cited

U.S. PATENT DOCUMENTS

| | | | |
|---|---|---|---|
| 3,072,249 | 1/1963 | Tritch | 206/441 |
| 4,646,831 | 3/1987 | Brower | 206/441 |
| 4,744,355 | 5/1988 | Faasse, Jr. | 206/441 |
| 4,753,232 | 6/1988 | Ward | 206/441 |
| 4,884,563 | 12/1989 | Sessions | 602/57 X |
| 4,909,244 | 3/1990 | Quarfout et al. | 602/57 X |
| 5,000,172 | 3/1991 | Ward | 602/57 |
| 5,060,642 | 10/1991 | Gilman | 602/57 |
| 5,106,629 | 4/1992 | Cartmell et al. | 602/57 |
| 5,115,801 | 5/1992 | Cartmell et al. | |
| 5,160,328 | 11/1992 | Cartmell et al. | 602/59 |
| 5,204,110 | 4/1993 | Cartmell et al. | 424/443 |
| 5,409,703 | 4/1995 | McAnalley et al. | 424/435 |
| 5,423,737 | 6/1995 | Cartmell et al. | 602/57 |

*Primary Examiner*—Richard J. Apley
*Assistant Examiner*—Kim M. Lee
*Attorney, Agent, or Firm*—Killworth, Gottman, Hagan & Schaeff

[57] ABSTRACT

A flexible, transparent wound dressing product contains a clear hydrogel material in a gel-like phase. The wound dressing product is comprised of several layers including a wound dressing, removable tab and release liner. The removable tab provides a grippable surface to allow for the removal of the release liner from the wound dressing and to facilitate handling of the wound dressing during application to the wound site. The tab may be comprised of a flat, double-coated paper or other suitable material, or a flexible, V-shaped member, and is removable by peeling after the wound dressing is applied. The wound dressing comprises a transparent thin-film layer, a first adhesive layer, backing layer, second adhesive layer, support layer and a hydrogel material. The transparent layer has a center portion and a perimeter portion. The backing layer, support layer and hydrogel material, which together form a reinforced hydrogel patch, are positioned in the center portion of the transparent layer. Since the wound dressing is transparent, a grid pattern may be printed on the backing layer to permit measurement of a wound. During manufacture, the hydrogel patch is assembled in sheet form and subsequently cut to a desired size and shape.

9 Claims, 5 Drawing Sheets

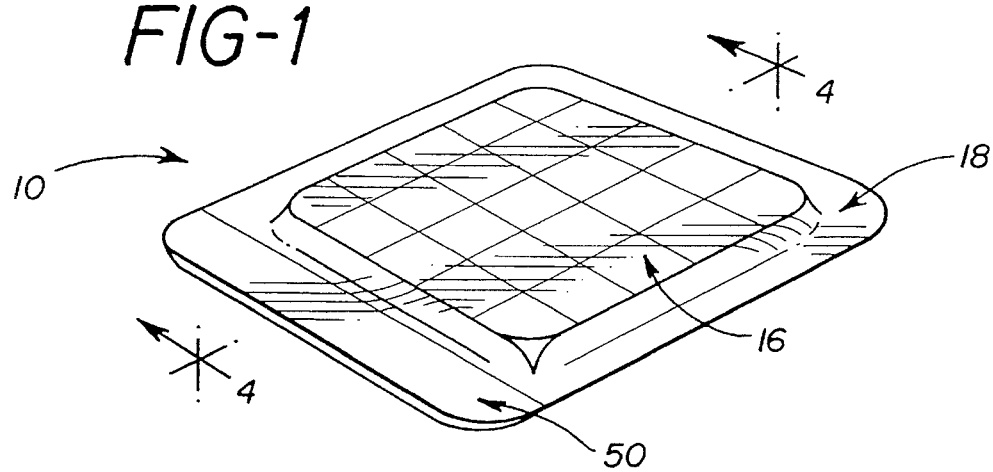
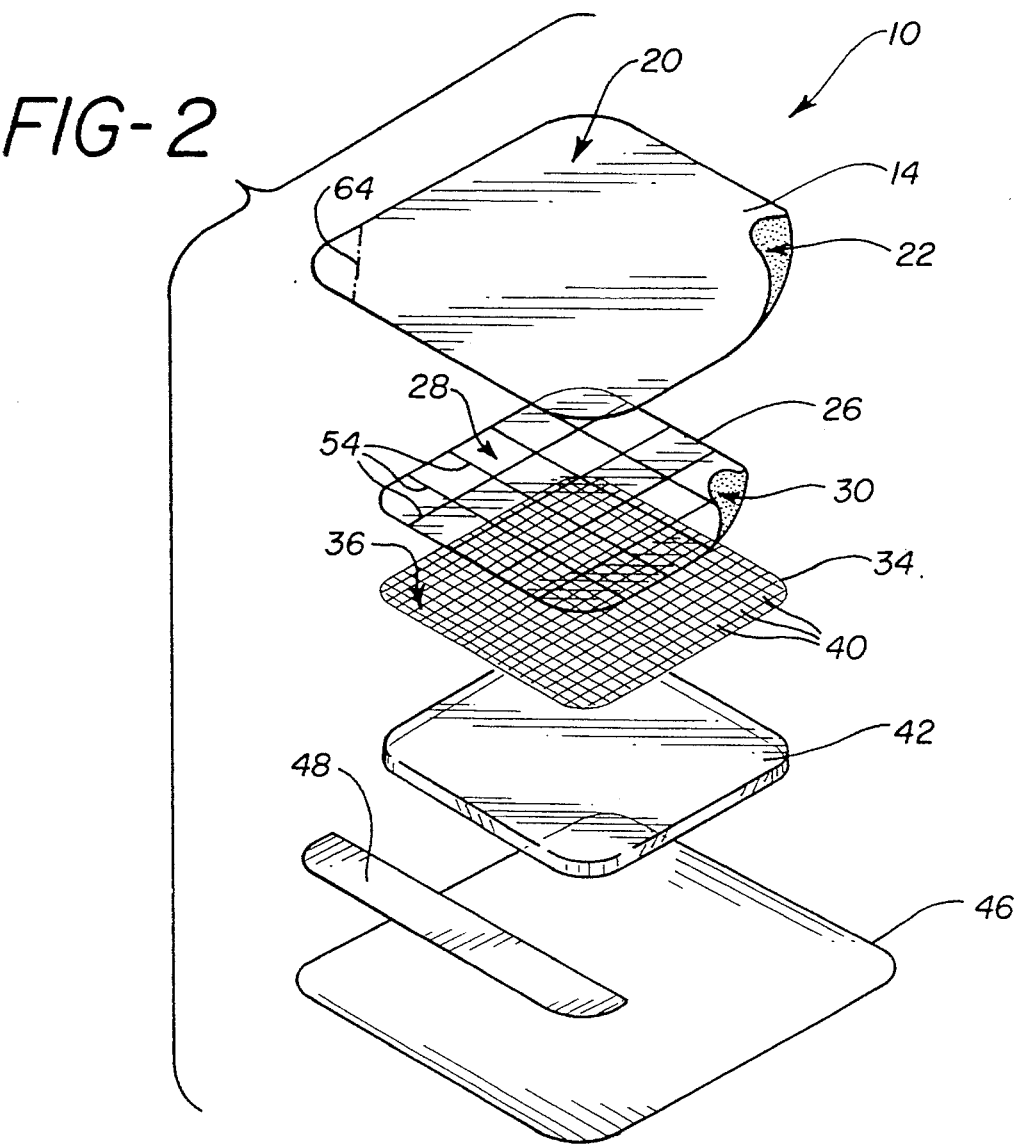

TRANSPARENT HYDROGEL WOUND DRESSING WITH RELEASE TAB

This application is a division of U.S. application Ser. No. 08/068,633 filed May 27, 1993, now U.S. Pat. No. 5,423,737.

BACKGROUND OF THE INVENTION

The present invention relates to wound dressings and, more particularly, to a transparent, flexible wound dressing product containing a hydrogel substance.

Secreting skin wounds, such as decubitus ulcers and open surgical wounds, have long presented a medical challenge in keeping such wounds sterile and relatively dry. The accumulation of wound exudate, such as blood, pustulation and other wound fluids, in wound crevices promotes growth of bacteria and crusted organisms which cause infection and delay the healing process. However, since it is often desirable to allow a wound to heal in a slightly moist or occlusive state, as it is believed that this may accelerate healing, excess wound exudate must be removed. If excess wound exudate remains on a wound, a "blister" of exudate can form under the wound dressing which is not only unsightly, but also may cause the dressing to leak, thereby defeating the aim of sterility. Existing methods of aspiration, however, can lead to wound infection or can destroy sterility. Additionally, it is not desirable to remove all exudate, as that would result in a dry wound and, hence, a slower healing process.

Known aqueous moisture-absorbing wound dressing systems have additional problems in that the aqueous material is generally contained in the center portion of a wound dressing, with a bulky adhesive border, such as a foam border. Problems with such borders include decreased comfort, conformity and adhesion, as well as the existence of a "lifting edge" that can catch on clothes or bed sheets, thereby exposing the wound to bacteria and infection. In addition, observation of the wound by medical personnel may require lifting the wound dressing, thereby exposing the wound, again creating a situation where bacteria and infection can be introduced to the wound site.

Adhesive wound dressings, similar to that disclosed by Ward, U.S. Pat. No. 4,753,232, issued Jun. 28, 1988, are frequently constructed of a polymer film having one adhesive surface. The polymer film is extremely thin and, therefore difficult to handle during application to the wound. Further, it is desirable to apply the wound dressing to the patient's skin without touching the surface of the dressing that is to come into contact with the skin. The prior art discloses several methods for facilitating handling of the wound dressing. Ward, for instance, discloses a "handle" portion along one edge of the dressing. After the dressing is applied, the handle may be removed by tearing, or it may carry an adhesive coating so that it may be adhered to the skin of the patient.

An existing method of avoiding contact with the edges of a bandage by fingers or forceps is disclosed in Brower, U.S. Pat. No. 4,646,731, issued Mar. 3, 1987. Brower discloses an adhesive-coated bandage whose edges are protected by a pair of folded V-shaped tabs. After the backing sheet is removed from the bandage, one tab is removed and the corresponding end of the bandage is applied to the skin. The second tab is grasped and removed as the entire length of the bandage is then applied.

Faasse, Jr., U.S. Pat. No. 4,744,355, issued May 17, 1988, solves a problem associated with excessive peeling force during removal of backings from wound dressings. The Faasse patent teaches a release liner adhesively attached to each end of a wound dressing strip (covering layer). A hinge arrangement is provided between each release liner and the dressing. As the release liners are pulled away from the wound dressing strip, the hinge means are employed, thus reducing the peeling force on the covering layer and preventing the liners from pulling away from the covering layer prematurely.

United Kingdom Patent Application No. 2,128,479 describes a surgical dressing with two release sheets, each covering half of the dressing and having a free edge curved at the center of the dressing. As the curved edges of the release sheets are peeled back, the center of the dressing is applied to the wound, followed by the ends, thereby preserving sterility by eliminating the need to touch the adhesive surface of the dressing.

European Patent Application Pub. No. 0 168 174 discloses a relatively rigid carrier section with bent handles over the outer surface of a thin-film dressing. The carrier section aids in keeping the dressing extended during application and prevents the ends from curling. The reference further discloses a tab portion along one edge of the dressing. This tab portion is not coated with adhesive. It may be grasped during application of the dressing to the patient's skin and is removable afterward by tearing.

Our own commonly-assigned U.S. Pat. No. 5,106,629, issued to Cartmell et al. on Apr. 21, 1992, discloses a hydrogel wound dressing with a thin-film transparent layer, a dimensionally stable backing layer over the outer surface of the transparent layer, and a release liner. The backing layer and the release liner each have a corner tab to facilitate the peeling of each from the transparent layer. The hydrogel material is positioned in a center portion of the transparent layer, and the adhesive perimeter portion of the transparent layer adheres to the skin of the patient. The dimensionally stable backing member prevents the transparent layer from curling and facilitates handling of the dressing during its application.

Only the Cartmell et al. reference discloses a wound dressing containing a hydrogel material for the absorption of wound exudate. Further, the means taught by the aforementioned references for facilitating the handling of a thin-film wound dressing layer are fairly complicated and may involve substantial expense in manufacture and materials, particularly when viewed in relation to the overall cost of the wound dressing.

It is seen, therefore, that there is a need for a hydrogel wound dressing product that may be easily handled during application to the wound without touching the adhesive side of the dressing. Further, there is a need for a hydrogel wound dressing product that is inexpensive and simple to manufacture, and easily removed from a release liner and applied to a wound.

SUMMARY OF THE INVENTION

The present invention meets these needs by providing a thin-film, transparent wound dressing containing a hydrogel material. The present invention also provides a method of manufacture of the wound dressing product. The wound dressing product herein can be manufactured to any desirable size to provide a thin-film, fluid-absorbing dressing for a wound of any size. The wound dressing herein is transparent, conformable and adhesive around its perimeter portion, and nonadhesive over the wound site.

The wound dressing product of the present invention comprises a release liner, removable tab, and wound dressing. The wound dressing comprises a transparent, preferably polyurethane, thin-film layer, a first adhesive layer, a backing layer, second adhesive layer, support layer and a hydrogel material. The transparent film layer, which may be of any suitable shape, but which typically is generally rectangular in shape, has a center portion and a perimeter portion surrounding the center portion, in addition to a first side and an opposing second side. When the dressing is applied to the wound, the first side of the transparent layer forms the outer surface of the dressing product. The transparent film layer may, alternatively, be constructed of materials other than polyurethane, such as polyethylene, vinyl, or other suitable materials, and may also be perforated throughout in order to allow the patient's skin to breathe.

The first adhesive layer is positioned on the second side of the transparent layer. The backing layer, preferably also constructed of a transparent polyurethane and having a first side and an opposing second side, is adhered to the second side of the transparent layer by means of the first adhesive layer. A second adhesive layer is positioned on the second side of the backing layer in order to accommodate the first side of the support layer. The support layer is made from a material such as woven and nonwoven fabrics, gauze, scrim or other similar materials. The hydrogel material is secured to the second side of the support layer. The permeable fabric of the support layer allows the hydrogel material to pass through to the first side of the support layer, resulting in the presence of the hydrogel layer on the first, as well as the second, side of the support layer.

The hydrogel material is preferably a saline solution in an aqueous gel-like phase, and is contained within the center portion of the transparent film. The gel-like consistency of the hydrogel material creates a bond between the wound dressing and the wound site without creating an actual adhesive attachment that would damage new cell tissue upon removal. An advantage of the gel-like hydrogel is that it will not deteriorate as the wound fluids are absorbed. Additionally, it permits clean and neat removal of the wound dressing when the wound heals or the dressing is changed.

The release liner, which is preferably silicone-coated, overlies the hydrogel material and is secured to the perimeter portion of the second side of the transparent layer by means of the first adhesive layer. The removable tab is interposed between the transparent layer and the release liner. The tab is adhered to one edge of the perimeter portion of the second side of the transparent layer by means of the first adhesive layer so as to provide a free grippable surface to allow for the removal of the release liner from the transparent layer and to facilitate the handling of the wound dressing during application of the dressing to the wound.

In a preferred embodiment of the present invention, the backing layer is printed with a grid pattern to allow medical personnel to monitor the healing of the wound, without removing the dressing, by measuring its size. A clear view of the wound is provided through the wound dressing, each layer of which is preferably transparent.

In one embodiment, the removable tab is flat and is constructed of double-coated paper, polystyrene, polyester, or other suitable material. In a second embodiment, the tab comprises a V-shaped member which is preferably silicone-coated. This V-shaped member has a first flap and a second flap, with the first flap being secured to the second side of the transparent layer by means of the first adhesive layer, and the second flap being positioned between the first flap and the release liner. The open end of the V-shaped member is positioned along one edge of the transparent layer and the opposing edge of the release liner. In both embodiments, the tab is removable by peeling after the wound dressing is applied to the patient's skin. The tab also aids in adding stability to the thin-film transparent layer as the release liner is removed from the transparent layer.

The present invention provides a method of manufacturing the wound dressing product. Initially, the transparent film is provided, preferably of a transparent polyurethane material. This film contains center and perimeter portions, along with a first side and an opposing second side. The second side of the transparent film is coated with a preferably medical-grade first adhesive layer. A backing layer is then provided, the second side of which is coated with a preferably medical-grade second adhesive layer. The first side of a support layer is laminated to the second side of the backing layer. The support layer comprises a material such as woven and nonwoven fabrics, gauze, scrim or other similar materials, and is permeable to the adhesive. A hydrogel material is then applied to the second side of the support layer. The interstices within the fabric of the support layer allow the hydrogel material to flow through to the first side of the support layer, such that the hydrogel layer resides on both the first and second sides of the support layer. Together, the backing layer, support layer and hydrogel material form a reinforced hydrogel patch.

Preferably, the hydrogel patch is manufactured in sheet form and cut to various sizes. The size of the transparent layer is selected accordingly in order that the center portion of the transparent layer is capable of accommodating the hydrogel patch. The hydrogel patch is then secured to the transparent layer such that the first side of the backing layer adheres to the center portion of the second side of the transparent layer by means of the first adhesive layer.

A release liner, preferably of a silicone-coated sheet material, is provided. A removable tab having first and second sides is also provided. The first side of the tab is laminated to one edge of the perimeter portion on the second side of the transparent layer, such that the first adhesive layer is positioned between the tab and the transparent layer. A first side of the release liner is then laminated to the perimeter portion on the second side of the transparent layer by means of the first adhesive layer. When the wound dressing product is fully assembled, the release liner overlies the hydrogel material and patch. In fact, the release liner, transparent layer and first adhesive layer form an adhesive seal around the hydrogel material, thus preserving sterility of the wound dressing.

In the preferred method of manufacture, a grid pattern is printed on the backing layer to enable medical personnel to measure the wound and monitor its healing. In one embodiment, a flat tab constructed of a double-coated paper is provided. Alternatively, a flat tab constructed of polystyrene, polyester, or other suitable material may be used. In a second embodiment, a tab comprising a V-shaped member is provided and is preferably silicone-coated. The V-shaped member has a first flap and a second flap, and the first flap is secured to the perimeter portion of the second side of the transparent layer by the first adhesive layer, while the second flap is positioned between the first flap and the release liner with the open end of the "V" positioned along one edge of the transparent layer and the opposing edge of the release liner. In both embodiments, this tab may be removed by peeling after the dressing is applied to the patient's skin.

It is an object of the present invention to provide a wound dressing product containing a hydrogel substance which is particularly advantageous when used to dress exuding wounds, such as decubitus ulcers, by providing a skin-like media which is biocompatible, nonirritating, fluid-absorbing, and bacterial-protective; to provide a wound dressing that is transparent, thereby allowing medical personnel to observe the healing progression of a wound without removing the wound dressing; to provide a wound dressing that is easily handled and applied to a wound without touching the adhesive portion of the dressing; and to provide a wound dressing that is less expensive to manufacture and has fewer materials than existing wound dressings.

Other objects and advantages of the invention will be apparent from the following description, the accompanying drawings and the appended claims.

BRIEF DESCRIPTION OF THE DRAWINGS

FIG. 1 is a perspective view of the wound dressing product.

FIG. 2 is an exploded perspective view, illustrating the layers which form a preferred embodiment of the wound dressing product.

DETAILED DESCRIPTION OF THE PREFERRED EMBODIMENTS

The present invention relates to a wound dressing product for application to a wound which includes a wound dressing comprised of a thin-film transparent layer and a hydrogel patch. The invention also includes a method of manufacture for the disclosed wound dressing product.

Referring to FIG. 1, the wound dressing product 10 of the present invention is shown. Although the wound dressing product 10 illustrated in FIG. 1 has a rectangular shape, it may be any of a variety of desired shapes. The wound dressing product 10 is composed of several layers, as illustrated by the exploded view of FIG. 2 and the exploded side view of FIG. 3.

Figure 3:
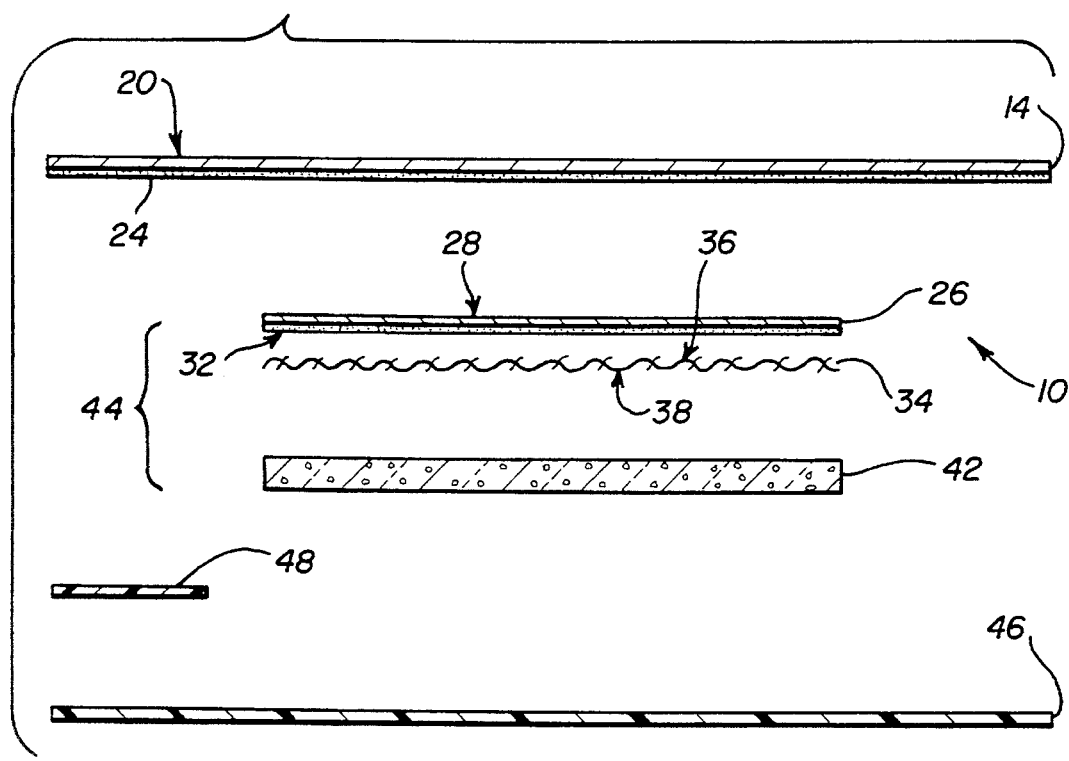
FIG. 3 is an exploded side view of the wound dressing product of FIG. 2.

Referring, collectively, to FIGS. 1, 2 and 3, the wound dressing product 10 includes a thin-film transparent layer 14, preferably of polyurethane, which has a center portion 16 and a perimeter portion 18. The transparent layer 14 has a first side 20 and a second side 22, the second side 22 being coated with a first adhesive layer 24. Backing layer 26, preferably constructed of a transparent polyurethane and having a first side 28 and a second side 30, is adhered to the second side 22 of transparent layer 14 by means of first adhesive layer 24. A second adhesive layer 32 is positioned on the second side 30 of backing layer 26 in order to accommodate first side 36 of a support layer 34. The support layer 34 is made from a material such as woven and nonwoven fabrics, gauze, scrim or other similar materials.

A hydrogel material 42 is adhered to the second side 38 of support layer 34. The permeable fabric of the support layer 34 contains interstices 40 which allow the hydrogel layer 42 to pass through to the first side 36 of support layer 34, resulting in the presence of hydrogel layer 42 on both the second side 38 and the first side 36 of support layer 34. The hydrogel material 42 is preferably a saline solution in an aqueous gel-like phase. The hydrogel material 42, support layer 34 and backing layer 26 together form a reinforced hydrogel patch 44, which is contained within the center portion 16 of transparent layer 14. A release liner 46, preferably of a silicone-coated sheet material, overlies the hydrogel material 42 and is secured to the perimeter portion 18 of the second side 22 of transparent layer 14 by means of first adhesive layer 24.

Figure 4:
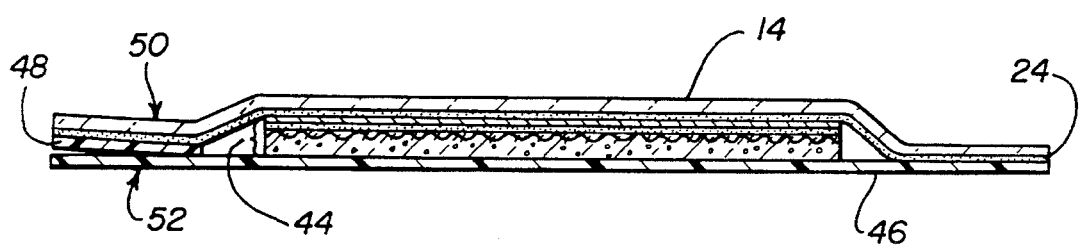
FIG. 4 is a cross-sectional view of the wound dressing product of FIG. 1 taken along line 4—4.
Figure 5:
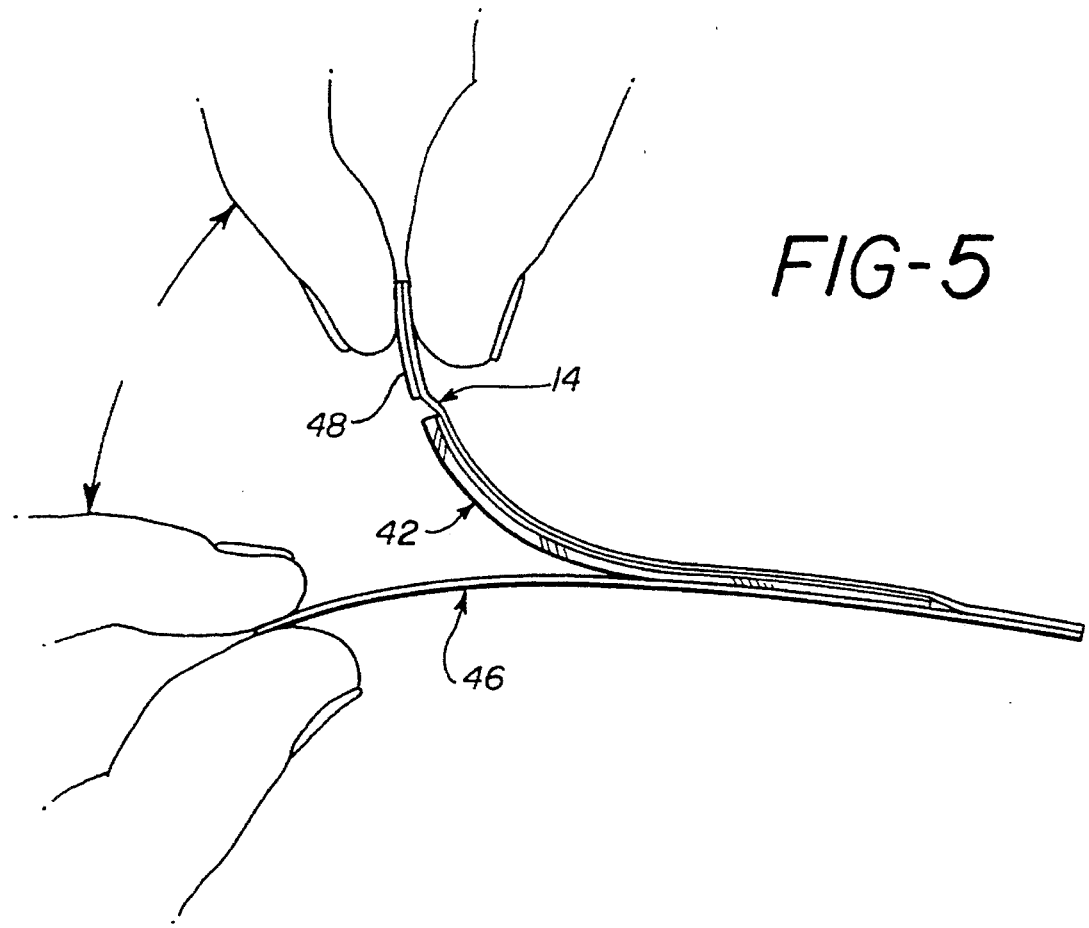
FIG. 5 is a side view of the wound dressing product which illustrates the peeling of the release liner from the wound dressing.
Figure 6:
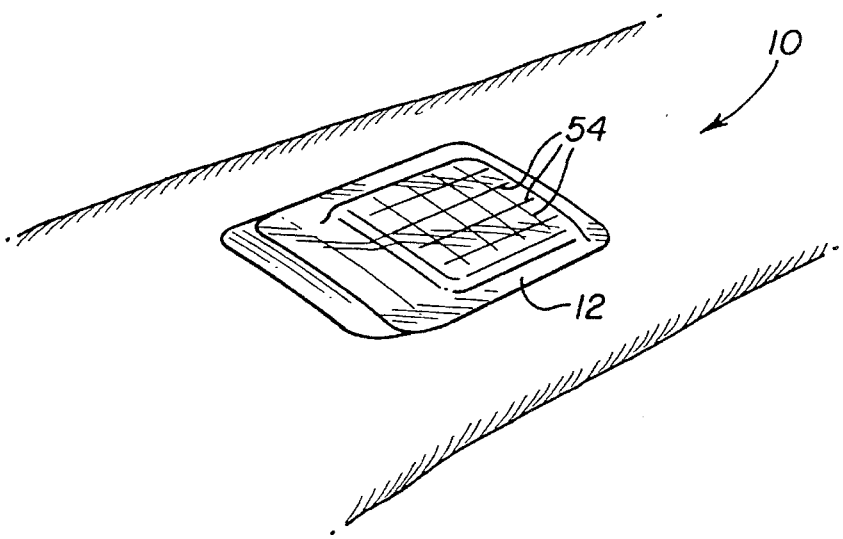
FIG. 6 is a perspective view showing the wound dressing in place on the patient's skin.

Referring now to FIGS. 4–6, collectively, a removable tab 48 is interposed between the transparent layer 14 and the release liner 46. The tab 48 is adhered to one edge 50 of the perimeter portion 18 of transparent layer 14 by means of the first adhesive layer 24, so as to provide a grippable surface to allow for the removal of the release liner 46 from transparent layer 14 and to facilitate the handling of the wound dressing 12 during application of the wound dressing 12 to the wound.

The gel-like consistency of the hydrogel material 42 creates a bond between the wound dressing 12 and the wound site without creating an actual adhesive attachment that would damage new cell tissue upon removal. An advantage of the gel-like hydrogel material 42 is that it will not deteriorate as the wound fluids are absorbed. Additionally, it permits clean and neat removal of the wound dressing 12 when the wound heals or the dressing 12 is changed.

In the preferred embodiment of the present invention, the backing layer 26 is printed with a grid pattern 54 to allow medical personnel to monitor the healing of the wound, without removing the wound dressing 12, by measuring its size. A clear view of the wound is provided through the dressing 12, each layer of which is preferably transparent. Although FIGS. 1, 2, 6 and 7 illustrate a rectangular grid pattern 54, any suitable grid pattern may be incorporated.

Figure 7:
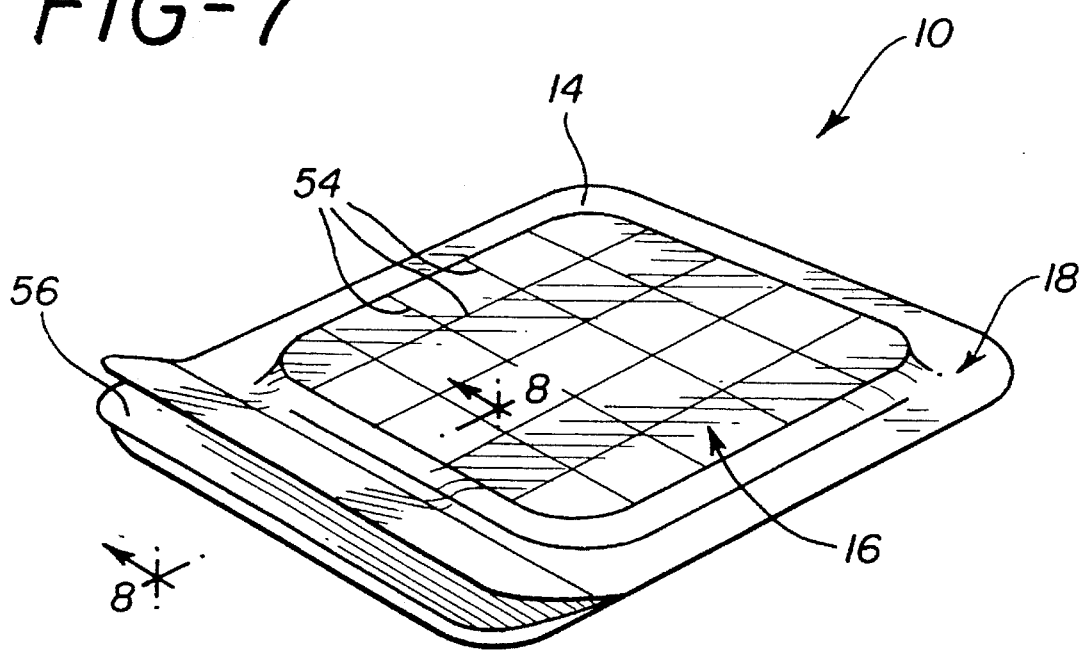
FIGS. 7 and 8 illustrate a second preferred embodiment in which the flat, polystyrene tab of FIGS. 1–6 is replaced with a V-shaped tab.
Figure 8:
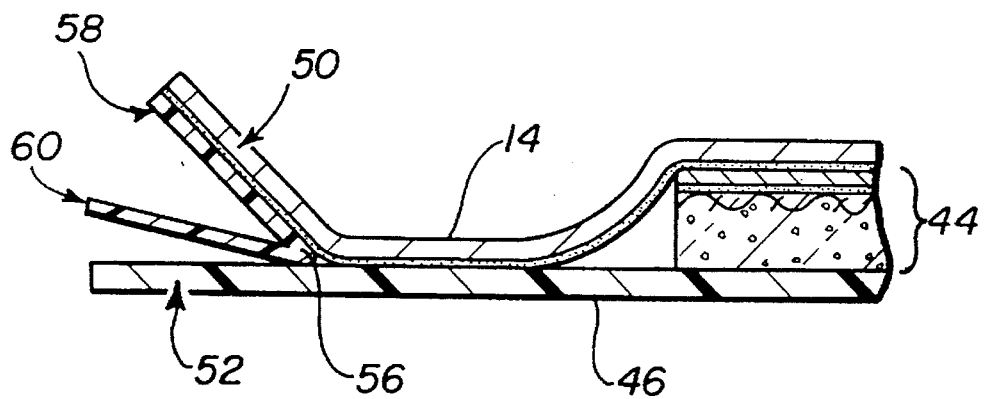

In one embodiment of the present invention, the removable tab 48 is constructed of a double-coated paper, polystyrene, polyester, or other suitable material, and is preferably flat, as shown in FIGS. 1–6. FIGS. 7 and 8 illustrate a second embodiment, wherein the flat tab 48 is replaced With a V-shaped member 56. The V-shaped member 56 has a first flap 58 and a second flap 60, with the first flap 58 being secured to one edge 50 of the second side 22 of transparent layer 14 by means of first adhesive layer 24, and the second flap 60 being positioned between first flap 58 and one edge 52 of release liner 46. The V-shaped member 56 and the release liner 46 are preferably coated with silicone. This enables the V-shaped member 56 to be more easily removed from the transparent layer 14, and enables the release liner 46 to be more easily removed from the transparent layer 14 and hydrogel material 42. Both the tab 48 and the V-shaped member 56 are removable by peeling after the wound dressing 12 is applied to the wound site. The tab 48 and V-shaped member 56 also aid in adding stability to the transparent layer 14 as release liner 46 is removed from the wound dressing product 10.

Figure 9A:
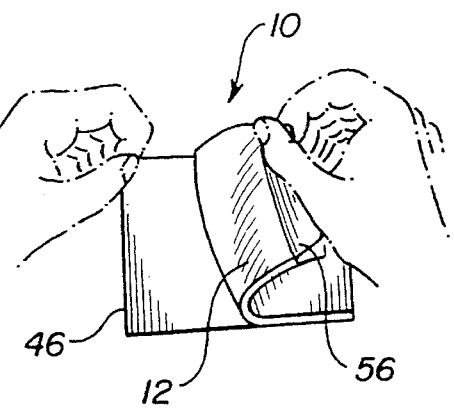
FIGS. 9A through 9D illustrate the preferred method of application of the wound dressing product of the present invention.
Figure 9B:
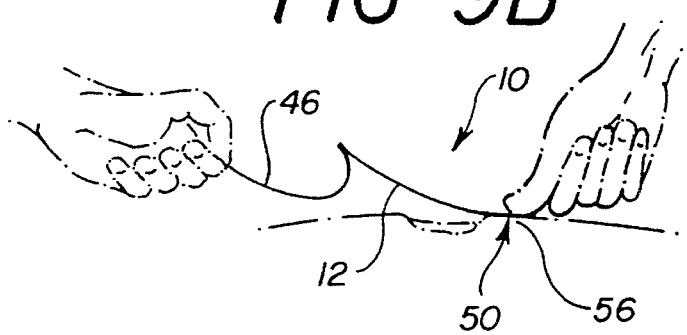
Figure 9C:
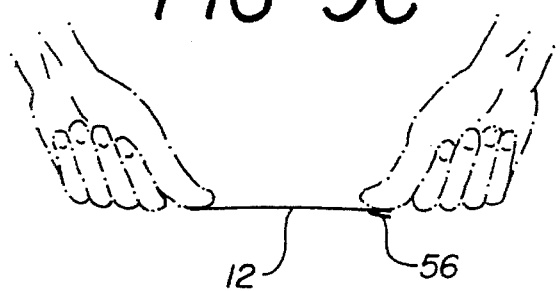
Figure 9D:
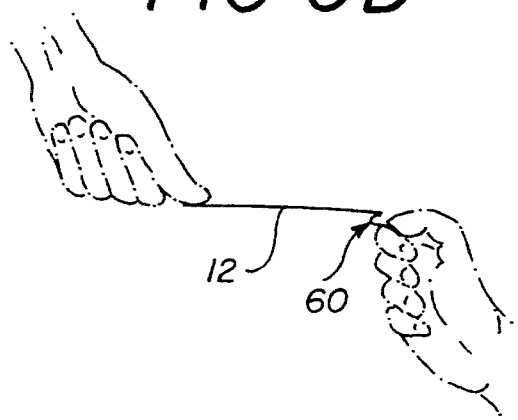

FIGS. 9A through 9D illustrate the preferred method of application of the wound dressing product 10 to a wound. Although these figures illustrate the application of a wound dressing 12 having a V-shaped member 56, a similar procedure may be used to apply the wound dressing 12 of FIGS. 2–5 wherein a flat tab 48 is utilized. As shown in FIG. 9A, the release liner 46 is first removed from the wound dressing 12 by grasping V-shaped member 56 and one edge 50 of transparent layer 14 with one hand, while grasping release liner 46 with the other hand. After the edge 50 of transparent layer 14 is removed from release liner 46, edge 50 is applied to the skin surrounding the wound of the patient. Edge 50 is then held in place while the release liner 46 is fully removed from wound dressing 12, as shown in FIG. 9B. After release liner 46 is removed, the wound dressing 12 is secured to the wound, as illustrated in FIG. 9C. As shown in FIG. 9D, V-shaped member 56 is then removed by pulling flap 60 with one hand while the opposite end of transparent film 14 of wound dressing 12 is held against the skin by the other hand.

The present invention also provides a method of manufacturing the wound dressing product 10. Initially, a transparent thin-film layer 14 is provided, preferably of a polyurethane material. Alternatively, transparent layer 14 may be constructed of polyethylene, vinyl, or any other suitable material, and may be perforated throughout to allow air to contact the skin of the patient. This transparent layer 14 contains a center portion 16 and a perimeter portion 18, along with a first side 20 and a second side 22. The second side 22 of the transparent layer 14 is coated with a preferably medical-grade first adhesive layer 24. A backing layer 26 is then provided, the second side 30 of which is coated with a preferably medical-grade second adhesive layer 32. The first side 36 of a support layer 34 is laminated to the second side 30 of the backing layer 26. The support layer 34 comprises a material such as woven and nonwoven fabrics, gauze, scrim or other similar materials. A hydrogel material 42 is then applied to the second side 38 of the support layer 34. The support layer 34 is permeable and contains interstices 40 within the fabric which allow the hydrogel layer 42—which, when applied to support layer 34, is in liquid form—to flow through to the first side 36 of the support layer 34, such that the hydrogel layer 42 resides on both the first side 36 and the second side 38 of the support layer 34. Together, the backing layer 26, support layer 34 and hydrogel material 42 form a reinforced hydrogel patch 44.

The hydrogel patch 44 is preferably assembled in a sheet form and subsequently cut into various pieces of desired size and shape. The size and shape of the transparent layer 14 are selected so as to accommodate the hydrogel patch 44. The hydrogel patch 44 is then laminated to the center portion 16 of transparent layer 14 such that the first side 28 of backing layer 26 adheres to the second side 22 of transparent layer 14 by means of first adhesive layer 24.

A release liner 46, preferably silicone-coated, is provided. A removable tab 48 having first and second sides is also provided. The first side of tab 48 is laminated to one edge 50 of the perimeter portion 18 on the second side 22 of transparent layer 14, such that the first adhesive layer 24 is positioned between tab 48 and transparent layer 14. A first side of release liner 46 is then laminated to the perimeter portion 18 on the second side 22 of transparent layer 14 by means of first adhesive layer 24. When the wound dressing product 10 is fully assembled, the release liner 46 overlies the hydrogel material 42 and hydrogel patch 44. In fact, the release liner 46, transparent layer 14 and first adhesive layer 24 form an adhesive seal around hydrogel material 42, thus preserving the sterility of the wound dressing product 10.

The preferred hydrogel material 42 is formed from an aqueous mixture including from about 0% to about 90% by weight polyhydric alcohol; from about 6% to about 60% by weight aliphatic diisocyanate-terminated prepolymer; from about 4% to about 40% by weight polyethylene oxide-based polyamine; up to about 2% by weight sodium chloride; and the balance water. A more preferred hydrogel composition for forming hydrogel layer 42 comprises from about 15% to about 30% by weight of a polyhydric alcohol selected from a group consisting of polypropylene glycol, polyethylene glycol and glycerine, from about 8% to about 14% by weight isophoronediisocyanate-terminated prepolymer, from about 5% to about 10% by weight polyethylene oxide-based diamine, up to about 1% by weight of a salt, and the remaining percentage water. Most preferably, the hydrogel material 42 includes 17% propylene glycol, 12% isophoronediisocyanate-terminated prepolymer, 9% polyethylene oxide-based diamine, 1% salt, and 61% water. The hydrogel material 42 provides a biocompatible, nonirritating, fluid-absorbing, bacterial-protective, cushioning, skin-like media over the wound site.

In the preferred method of manufacture, a grid pattern 54 is printed on backing layer 26 to enable medical personnel to measure the wound and monitor its healing. Those skilled in the art will recognize that a similar grid pattern could be printed on the transparent layer 14, rather than on the backing layer 26, without deviating from the invention. In one embodiment, a flat tab 48, constructed of a double-coated paper, polystyrene, polyester, or any other suitable material, is provided. This first embodiment may further include a transparent layer 14 having a cropped corner 64, as represented by the phantom line drawn in FIG. 2, at the edge 50 of the perimeter portion 18, in order to facilitate removal of the tab 48 from transparent layer 14 after wound dressing 12 is applied to the wound. In a second embodiment, a V-shaped member 56, preferably silicone-coated, is provided in place of flat tab 48. The V-shaped member 56 has a first flap 58 and a second flap 60. The first flap 58 is secured to the second side 22 of the transparent layer 14 by first adhesive layer 24, while the second flap 60 is positioned between the first flap 58 and release liner 46. The open end of the "V" is positioned along one edge 50 of transparent layer 14 and the opposing edge 52 of release liner 46. Both the tab 48 and the V-shaped member 56 are removable by peeling after the wound dressing 12 is applied to the patient's skin.

The wound dressing product 10 of the present invention is particularly advantageous for use on exuding wounds. In particular, a special feature of the hydrogel material 42 is that it is sufficiently clear and transparent that visual observation of the wound is possible without removal of the wound dressing 12. Another benefit of the hydrogel material 42 is that it retains its gel-like integrity even upon removal of the wound dressing 12 from a wound site. The hydrogel material 42 does not leave debris in the wound when the wound dressing 12 is removed, nor does it adhere to the wound site. The benefit of this feature is that the hydrogel material 42 exhibits a capability of nontraumatically releasing from the wound when the wound dressing 12 is removed, so as to not destroy new cell tissue forming at the wound site. Thus, healing is not inhibited by removal of the dressing 12.

Having described the invention in detail and by reference to preferred embodiments thereof, it will be apparent that modifications and variations are possible without departing from the scope of the invention which is defined in the appended claims.

What is claimed is:

1. A method of manufacturing a wound dressing product for a wound, comprising the steps of:

providing a transparent thin-film layer having a first side and a second side and further having a perimeter portion and a center portion;

coating said perimeter portion of said second side of said transparent layer with a first adhesive layer;

providing a backing layer having a first side and a second side;

coating said second side of said backing layer with a second adhesive layer;

providing a support layer having a first side and a second side, said support layer comprising a permeable fabric having a plurality of interstices therewithin;

laminating said first side of said support layer to said second side of said backing layer;

applying a hydrogel material to said second side of said support layer, wherein said hydrogel material penetrates said interstices to said first side of said support layer such that said hydrogel material resides on both said first side and said second side of said support layer, and whereby said backing layer, said support layer and said hydrogel material collectively form a reinforced hydrogel patch;

laminating said hydrogel patch to said center portion of said transparent layer, wherein said first side of said backing layer adheres to said second side of said transparent layer by means of said first adhesive layer;

providing a release liner having a first side and a second side;

providing at least one removable tab having a first side and a second side, so as to provide a grippable surface to facilitate the removal of said release liner from said transparent layer and to facilitate the handling of said wound dressing during application of said dressing to a wound;

laminating said first side of said tab to one edge of said perimeter portion of said second side of said transparent layer, whereby said first adhesive layer is positioned between said tab and said transparent layer;

laminating said first side of said release liner to said perimeter portion of said second side of said transparent layer, whereby said adhesive layer is positioned between said transparent layer and said release liner, and said tab portion is positioned between said adhesive layer and said release liner.

2. A method of manufacturing a wound dressing product as claimed in claim 1, wherein the step of providing a backing layer comprises the step of providing a transparent backing layer.

3. A method of manufacturing a wound dressing product as claimed in claim 2, further including the step of printing a grid pattern on said backing layer.

4. A method of manufacturing a wound dressing product as claimed in claim 1, wherein said reinforced hydrogel patch is formed in a sheet and cut to a desired size, and the size of said transparent layer is selected so as to accommodate said hydrogel patch.

5. A method of manufacturing a wound dressing product as claimed in claim 1, in which the step of providing a removable tab includes the step of providing a removable tab comprising double-coated paper.

6. A method of manufacturing a wound dressing product as claimed in claim 1, in which the step of providing a removable tab includes the step of providing a tab comprising a V-shaped member having a first flap and a second flap, said first flap secured to said second side of said transparent layer by means of said first adhesive layer, said second flap positioned between said first flap and said release liner, and the open end of said V-shaped member positioned along said edge of said transparent layer and the opposing edge of said release liner.

7. A method of manufacturing a wound dressing product as recited in claim 1, wherein said hydrogel material comprises:

(a) from about 0% to about 90% by weight polyhydric alcohol;

(b) from about 6% to about 60% by weight aliphatic diisocyanate-terminated prepolymer;

(c) from about 4% to about 40% by weight polyethylene oxide-based polyamine;

(d) up to about 2% by weight sodium chloride; and (e) the balance water.

8. A method of manufacturing a wound dressing product as recited in claim 1, wherein said hydrogel material comprises:

(a) from about 15% to about 30% by weight polyhydric alcohol;

(b) from about 8% to about 14% by weight isophorone diisocyanate-terminated prepolymer;

(c) from about 5% to about 10% by weight polyethylene oxide-based diamine;

(d) up to about 1% by weight sodium chloride; and (e) the balance water.

9. A method of manufacturing a wound dressing product as recited in claim 1, wherein said hydrogel material comprises:

(a) about 17% by weight polypropylene glycol;

(b) about 12% by weight isophorone diisocyanate-terminated prepolymer;

(c) about 9% by weight polyethylene oxide-based diamine;

(d) about 1% by weight sodium chloride; and (e) about 61% by weight water.

* * * * *